United States Patent [19]

Corriu et al.

[11] Patent Number: 4,835,316
[45] Date of Patent: May 30, 1989

[54] NEW ORGANOMAGNESIUM COMPLEXES IN SOLID FORM, PROCESS FOR THEIR PREPARATION, AND THEIR USE

[75] Inventors: Robert Corriu; Genevieve Cerveau, both of Montpellier; Claude Chuit, Junas; Catherine Reye, Montpellier; Alain Boudin, Clermont L'Herault, all of France

[73] Assignee: Rhone-Poulenc Chimie, Courbevoie, France

[21] Appl. No.: 103,642

[22] Filed: Oct. 2, 1987

[30] Foreign Application Priority Data

Oct. 3, 1986 [FR] France .................................. 86 13809

[51] Int. Cl.$^4$ .................. C07C 93/04; C07F 3/02
[52] U.S. Cl. ........................... 564/505; 564/346; 260/665 G
[58] Field of Search ............... 564/505, 346; 260/665 G

[56] References Cited

U.S. PATENT DOCUMENTS 4,434,745 8/1982 Soula ..................................... 556/95

FOREIGN PATENT DOCUMENTS 0016673 10/1980 European Pat. Off. .

OTHER PUBLICATIONS

Grant and Hackh's Chemical Dictionary, 5th Edition, p. 270.
Jerry March, "Advance Organic Chemistry", 3rd Ed., pp. 157–160 and p. 559.

*Primary Examiner*—Prince E. Willis
*Assistant Examiner*—Christine A. Skane

*Attorney, Agent, or Firm*—Finnegan, Henderson, Farabow, Garrett & Dunner

[57] ABSTRACT

Organgomagnesium complexes which correspond to the formula (I): ps
$$(RMgX)_m/N[-CHR_1-CHR_2-O-(CHR_3-CHR_4-O)_n-R_5]_3 \quad (I)$$

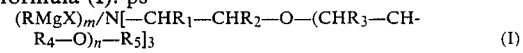

wherein:
  m is 1, 2, or 3;
  R denotes a substituted or unsubstituted group which is:
    linear or branched alkyl containing from 1 to 18 carbon atoms,
    alkenyl or alkynyl containing from 2 to 18 carbon atoms,
    cycloalkyl or cycloalkenyl containing from 3 to 12 carbon atoms,
    alkoxyalkyl, dialkoxyalkyl or alkylthiocarbonyl, aryl (which aryl may particularly be position-substituted by at least a halogen or an alkoxy, trifluoroemethyl, trifluoromethoxy or trifluromethoylthio group), or
    alkoxyaryl or alkylthioaryl;
  X denotes a chlorine, iodine or bromine atom;
  n is an integer ranging from 0 to about 10;
  $R_1$, $R_2$, $R_3$ and $R_4$, which are identical or different, denote a hydrogen atom or an alkyl or cycloalkyl radical containing from 1 to 4 carbon atoms; and
  $R_5$, which is identical or different in each of the three $[-CHR_1-CHR_2-O-(CHR_3-CHR_4-O)$ hd $n-R_5]$ chains, denotes an alkyl or cycloalkyl radical containing 1 to 12 carbon atoms, a phenyl radical or a radical of formula $-C_pH_{2p}-\phi$ or $C_pH_{(2p+1)}-\phi-$, wherein p ranges from 1 to about 12.

15 Claims, No Drawings

NEW ORGANOMAGNESIUM COMPLEXES IN SOLID FORM, PROCESS FOR THEIR PREPARATION, AND THEIR USE

The present invention relates to new organomagnesium complexes, the process for their preparation and their applications.

Organomagnesium complexes are useful for the synthesis of new organic products, especially for the formation of new carbon-carbon bonds. It is known to prepare organomagnesium complexes. However, these highly reactive compounds, which sometimes are even very violent, are only stable and capable of being transported as a solution in ether or in ether-containing solvents. This presents major safety problems on an industrial scale. Given the instability heretofore associated with such complexes, it has thus been necessary to manufacture them at the time they are required for use.

The purpose of the present invention is to remedy the disadvantages of the extemporaenous preparation of organomagnesium complexes. The present invention can provide solid organomagnesium compounds which are stable and capable of being stored in a directly marketable form. The present invention relates to new solid organomagnesium complexes which correspond to the formula (I):

$$(RMgX)_m / N[-CHR_1-CHR_2-O-(CHR_3-CHR_4-O)_n-R_5]_3 \quad (I)$$

wherein:
m is 1, 2 or 3;
R denotes a substituted or unsubstituted group selected from the group consisting of:
  linear or branched alkyl containing from 1 to 18 carbon atoms,
  alkenyl or alkynyl containing from 2 to 18 carbon atoms,
  cycloalkyl or cycloalkenyl containing from 3 to 12 carbon atoms, and
  alkoxyalkyl, dialkoxyalkyl, alkylthioalkyl, aryl (which aryl may be substituted, for example, by at least a halogen, alkyl, alkoxy, trifluoromethyl, trifluoromethoxy or trifluoromethylthio group), alkoxyaryl or alkylthioaryl;
X denotes a chlorine, iodine or bromine atom;
n is an integer varying from 0 to about 10;
$R_1$, $R_2$, $R_3$ and $R_4$, which are identical or different, denote a hydrogen atom or an alkyl or cycloalkyl radical containing 1 to 4 carbon atoms; and
$R_5$, which is identical or different in each of the three [$-CHR_1-CHR_2-O-(CHR_3-CHR_4-O)_n-R_5$] chains, denotes an alkyl or cycloalkyl radical containing 1 to 12 carbon atoms, a phenyl radical or a radical of formula $-C_pH_{2p}-\phi-$ or $C_pH_{(2p+1)}-\phi-$, wherein p ranges from 1 to about 12.

The preferred compounds are those in which at least one of the following criteria is met:
  R denotes a phenyl, alkyl or alkenyl group containing at least 3 carbon atoms, substituted if desired by an alkoxy, dialkoxy, alkylthio or phenyl group;
  $R_1$, $R_2$, $R_3$ and $R_4$, which are identical or different, denote a hydrogen atom or a methyl radical;
  n is equal to 0, 1, 2 or 3; and
  $R_5$ denotes an alkyl group containing 1 to 4 carbon atoms.

Preferred complexing agents include:
tris(3-oxabutyl)amine of the formula:

$$N(CH_2-CH_2-O-CH_3)_3,$$

tris(3-oxaheptyl)amine of the formula:

$$N(CH_2-CH_2-O-C_4H_9)_3,$$

tris(3,6-dioxaheptyl)amine of the formula:

$$N(CH_2-CH_2-O-CH_2-CH_2-O-CH_3)_3,$$

tris(3,6,9-trioxadecyl)amine of the formula:

$$N(CH_2-CH_2-O-CH_2-CH_2-O-CH_2-CH_2-O-CH_3)_3,$$

tris(3,6-dioxaoctyl)amine of the formula:

$$N(CH_2-CH_2-O-CH_2-CH_2-O-C_2H_5)_3,$$

tris(3,6,9-trioxaundecyl)amine of the formula:

$$N(CH_2-CH_2-O-CH_2-CH_2-O-CH_2-CH_2-O-C_2H_5)_3,$$

tris(3,6-dioxanonyl)amine of the formula:

$$N(CH_2-CH_2-O-CH_2-CH_2O-C_3H_7)_3,$$

tris(3,6,9-trioxadodecyl)amine of the formula:

$$N(CH_2-CH_2-O-CH_2-CH_2-O-CH_2-CH_2-O-C_3H_7)_3,$$

tris(3,6-dioxadecyl)amine of the formula:

$$N(CH_2-CH_2-O-CH_2-CH_2-O-C_4H_9)_3,$$

tris(3,6,9-trioxatridecyl)amine of the formula:

$$N(CH_2-CH_2-O-CH_2-CH_2-O-CH_2-CH_2-O-C_4H_9)_3,$$

tris(3,6,9,12-tetraoxatridecyl)amine of the formula:

$$N(CH_2-CH_2-O-(CH_2-CH_2-O-)_3-CH_3)_3,$$

tris(3,6-dioxa-4-methylheptyl)amine of the formula:

$$N(CH_2-CH_2-O-CHCH_3-CH_2-O-CH_3)_3,$$
and tris(3,6-dioxa-2,4-dimethylheptyl)amine of the formula:

$$N(CH_2-CHCH_3-O-CHCH_3-CH_2-O-CH_3)_3.$$

The compounds of the formula:

$$RMgX/N(CH_2-CH_2-O-CH_2-CH_2-O-CH_3)_3$$

in which R and X have the same meaning as defined above for formula (I) are particularly preferred.

The new organomagnesium complexes of the present invention are prepared, in particular, by a reaction of the complexing agent of formula:

$$N[-CHR_1-CHR_2O-(CHR_3-CHR_4-O)_n-R_5]_3,$$

wherein $R_1$, $R_2$, $R_3$, $R_4$, $R_5$ and n are as defined above for formula (I), with the organomagnesium compound of formula RMgX, wherein R and X are as defined above, in an anhydrous solvent and under an inert atmosphere.

According to a preferred method of preparing the compounds which are the subject of the invention, the complexing agent, followed by the organomagnesium compound is introduced into a solvent that is preferably an ether-containing solvent. The complexed organomagnesium compound precipitates and is recovered by any means known to the person skilled in the art. The compound can be dried under vacuum and stored, preferably under an inert gas, such as nitrogen. Advantageously, the organomagnesium compound is contacted with the complexing agent at ambient temperature.

When the complexes of the invention are being prepared, it is generally preferable to operate with an excess of the organomagnesium compound. A molar ratio of the organomagnesium compound to the complexing agent of greater than 1, preferably at least 2, is often preferred.

Other characteristics and advantages will become apparent during the detailed description of the invention, supplemented by the examples of implementation which do not imply any limitation on the invention.

The organomagnesium complex may be synthesized under a neutral atmosphere, such as nitrogen. A solution of three equivalents of RMgX in ethyl ether is placed in a Schlenk tube with stirring. One equivalent of the complexing agent, diluted with approximately an equal volume of ethyl ether, is added dropwise at ambient temperature. Immediately upon addition, a white precipitate forms. At the end of the addition, this precipitate changes to a paste.

The pasty solid residue is filtered off, washed with anhydrous ether and dried under vacuum for 2 hours. In this manner, a white powder is produced and stored under nitrogen.

Quantitative analysis of this powder establishes that it contains 1 to 2 mmoles of organomagnesium compound RMgX per gram. Quantitative analysis of the ether wash and the filtrate contain the remainder of the organomagnesium compound.

It is also possible to employ, as a starting material, an organomagnesium compound in solution in tetrahydrofuran (THF). If so, it will be advantageous to increase the dilution of the complexing agent.

The powders obtained can be stable up to approximately 120° C.

The present invention also relates to the use of the complex of formula I as a Grignard reagent for synthesizing new organic compounds by the formation of new carbon-carbon bonds. For this purpose, a complex of formula I may be reacted with a carbonyl compound in an organic solvent. Ketones, aldehydes, esters, acid chlorides and acid anhydrides are examples of useful carbonyl compounds.

Ethyl ether, tetrahydrofuran, petroleum ether, cyclohexane, toluene, acetonitrile, the alkanes, dimethylacetamide, hexamethylphosphoramide and dimethylformamide are illustrative solvents that can be employed.

Compared to the uncomplexed organomagnesium reactants or Grignard reagents, the organomagnesium complexes generally react more slowly with carbonyl compounds. Thus, depending on the reaction temperature, the organomagnesium complex of the invention may be reacted with one functional group and not with another when a multifunctional condensing agent, such as one containing both an aldehyde group and an ester group, is employed.

The examples below serve to illustrate the use of the compounds according to the invention; they are not to be regarded in any event as limiting the invention.

TABLE I

Example I: Reaction of RMgX/tris(3,6-dioxaheptyl)amine with ketones

| R | X | Reactant | Solvent | Operating conditions | Yield | Product formed |
|---|---|---|---|---|---|---|
| Phenyl | Br | $\phi$-C(=O)CH$_3$ | Petroleum ether | 70° C./4 hours | 80% | $\phi$-C(OH)(CH$_3$)($\phi$)[1] |
| Phenyl | Br | $\phi$-C(=O)CH$_3$ | Cyclohexane | 60° C./4 hours | 60% | $\phi$-C(OH)(CH$_3$)($\phi$)[1] |
| Phenyl | Br | $\phi$-C(=O)CH$_3$ | Toluene | 60° C./4 hours | 80% | $\phi$-C(OH)(CH$_3$)($\phi$)[1] |
| Allyl | Br | $\phi$-C(=O)CH$_3$ | Petroleum ether | 55° C./4 hours | 100% | CH$_2$=CH-CH$_2$-C(OH)(CH$_3$)($\phi$)[1] |
| Isopropyl | Br | $\phi$-C(=O)CH$_3$ | Petroleum ether | 70° C./4 hours | 60% | (CH$_3$)$_2$CH-C(OH)(CH$_3$)($\phi$)[1] |

TABLE I-continued

Example I: Reaction of RMgX/tris(3,6-dioxaheptyl)amine with ketones

| R | X | Reactant | Solvent | Operating conditions | Yield | Product formed |
|---|---|---|---|---|---|---|
| n-Butyl | Br | φ-C(=O)CH₃ | Petroleum ether | 70° C./4 hours | 80% | (n-Bu)(φ)(CH₃)C—OH [1] |
| Ethyl | Br | φ-C(=O)CH₃ | Ethyl ether | 20° C./1 hour | | (Et)(φ)(CH₃)C—OH [1] |
| Ethyl | Br | φ-C(=O)CH₃ | THF | −35° C./15 min | | (Et)(φ)(CH₃)C—OH [1] |

[1] After hydrolysis

TABLE II

Example II: Reaction of RMgX/tris(3,6-dioxaheptyl)amine with esters

| R | X | Reactant | Solvent | Operating conditions | Yield | Product formed |
|---|---|---|---|---|---|---|
| Ethyl | Br | Ethyl benzoate | THF | 20° C./1 hour | 100% | φ-C(OH)(Et)(Et) |
| φ | Br | Ethyl chloroformate | Ethyl ether | 20° C./12 hours | 45% | φ-C(=O)OEt |
| n-Heptyl | Br | Ethyl chloroformate | Ethyl ether | 20° C./12 hours | 45% | nHept-C(=O)OEt |
| φ | Br | Ethyl chloroformate | TAF | −15° C./1 hour | 94% | φ-C(=O)OEt |
| n-Butyl | Br | Ethyl chloroformate | TAF | −15° C./1 hour | 30% | n-Bu-C(=O)OEt |

TABLE III

Example III: Reaction of RMgX/tris(3,6-dioxaheptyl)amine with acid chlorides

| R | X | Reactant | Solvent | Experimental conditions | Yield | Product formed |
|---|---|---|---|---|---|---|
| Ethyl | Br | Benzoyl chloride | THF | 0° C. | 80% | φ-C(=O)-φ |

We claim:

1. A solid organomagnesium complex of the formula (I):

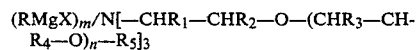
(I)

wherein:
m is 1, 2 or 3;

R denotes a substituted or unsubstituted group selected from the group consisting of:
  linear or branched alkyl containing from 1 to 18 carbon atoms,
  alkenyl or alkynyl containing from 2 to 18 carbon atoms,
  cycloalkyl or cycloalkenyl containing from 3 to 12 carbon atoms, and
  alkoxyalkyl, dialkoxyalkyl, alkylthiocarbonyl, aryl, alkoxyaryl or alkylthioaryl;

X denotes a chlorine, iodine or bromine atom;

n is an integer ranging from 0 to about 10, $R_1$, $R_2$, $R_3$ and $R_4$, which are indentical or different, denote a hydrogen atom or an alkyl or cycloalkyl radical containing from 1 to 4 carbon atoms; and $R_5$, which is identical or different in each of the three [—$CHR_1$—$CHR_2$—O—($CHR_3$—$CHR_4$—O)-$n$—$R_5$] chains, denotes an alkyl or cycloalkyl radical containing 1 to 12 carbon atoms, a phenyl radical or a radical of the formula $-C_pH_{2p}-$phenyl or $C_pH_{(2p+1)}-$phenyl—, wherein p ranges from 1 to about 12.

2. The solid complex of claim 1, wherein R is aryl substituted by at least one group selected from the group consisting of halogen, alkoxy, trifluoromethyl, trifluoromethoxy and trifluoromethylthio.

3. The solid complex of claim 1, wherein R denotes an alkyl or alkenyl group containing at least 3 carbon atoms.

4. The solid complex of claim 3, wherein R is substituted by at least one group selected from the group consisting of alkoxy, dialkoxy, alkylthio and phenyl.

5. The solid complex of claim 1, wherein $R_1$, $R_2$, $R_3$ and $R_4$, which are identical or different, denote a hydrogen atom or a methyl radical.

6. The solid complex of claim 1, wherein n is equal to 0, 1, 2 or 3.

7. The solid complex of claim 1, wherein $R_5$ denotes an alkyl group containing 1 to 4 carbon atoms.

8. The solid complex of claim 1, which corresponds to the formula:

$$(RMgX)_m/N(-CH_2-CH_2-O-CH_2-CH_2-O-CH_3)_3,$$

wherein m, R and X are as defined in claim 1.

9. A process for the preparation of the solid complex of claim 1, comprising the step of contacting an organomagnesium compound of the formula RMgX with a complexing agent of the formula:

$$N[-CHR_1-CHR_2-O-(CHR_3-CHR_4-O)_n-R_5]_3,$$

wherein R, X, $R_1$, $R_2$, $R_3$, $R_4$, $R_5$ and n are as defined in claim 1, in an anhydrous solvent and under an inert atmosphere.

10. The process of claim 9, wherein the anhydrous solvent is ethyl ether or tetrahydrofuran.

11. The process of claim 9, wherein the molar ratio of the organomagnesium compound to the complexing agent is greater than 1.

12. The process of claim 9, wherein the complexing agent is employed in solution in ethyl ether or tetrahydrofuran.

13. A compound formed by reacting the solid complex of formula I of claim 1 with a carbonyl compound in an organic solvent.

14. The compound of claim 13, wherein the carbonyl compound is selected from the group consisting of ketones, aldehydes, esters, acid chlorides and acid anhydrides.

15. The compound of claim 13, wherein the organic solvent is selected from the group consisting of ethyl ether, tetrahydrofuran, petroleum ether, cyclohexane, toluene, acetonitrile, the alkanes, dimethylacetamide, hexamethylphosphoramide and dimethylformamide.

* * * * *

UNITED STATES PATENT AND TRADEMARK OFFICE
CERTIFICATE OF CORRECTION

PATENT NO. : 4,835,316

DATED : May 30, 1989

INVENTOR(S) : Robert Corriu et al.

It is certified that error appears in the above-identified patent and that said Letters Patent is hereby corrected as shown below:

In the section entitle "ABSTRACT"

line 2, delete "ps";

line 19, delete "fluromethoylthio" and replace it with --fluoromethylthio--;

line 23, delete "di fferent" and replace it with --different--; and line 27, delete "hd" and replace it with -- - --.

Signed and Sealed this

Eleventh Day of September, 1990

Attest:

HARRY F. MANBECK, JR.

*Attesting Officer*      *Commissioner of Patents and Trademarks*